(12) United States Patent
Hytönen et al.

(10) Patent No.: US 7,932,415 B2
(45) Date of Patent: Apr. 26, 2011

(54) PROCESS FOR MANUFACTURING ENTACAPONE

(75) Inventors: Martti Hytönen, Helsinki (FI); Leif Hilden, Kauniainen (FI)

(73) Assignee: Orion Corporation, Espoo (FI)

( * ) Notice: Subject to any disclaimer, the term of this patent is extended or adjusted under 35 U.S.C. 154(b) by 338 days.

(21) Appl. No.: 12/278,043

(22) PCT Filed: Feb. 6, 2007

(86) PCT No.: PCT/FI2007/000029
§ 371 (c)(1),
(2), (4) Date: Sep. 4, 2008

(87) PCT Pub. No.: WO2007/090923
PCT Pub. Date: Aug. 16, 2007

(65) Prior Publication Data
US 2009/0012176 A1    Jan. 8, 2009

Related U.S. Application Data

(60) Provisional application No. 60/765,196, filed on Feb. 6, 2006.

(51) Int. Cl.
*C07C 225/00* (2006.01)
(52) U.S. Cl. ...................................................... 558/401
(58) Field of Classification Search ................... 558/401
See application file for complete search history.

(56) References Cited

U.S. PATENT DOCUMENTS

| 5,135,950 A | 8/1992 | Pippuri et al. |
| 5,446,194 A * | 8/1995 | Backstrom et al. ........... 558/401 |
| 2006/0258877 A1 | 11/2006 | Deshpande et al. |

FOREIGN PATENT DOCUMENTS

| GB | 2 200 109 A | 7/1988 |
| WO | WO 2005/070881 A1 | 8/2005 |

OTHER PUBLICATIONS

International Search Report dated May 25, 2007 for International Application No. PCT/FI2007/000029.
Written Opinion for International Application No. PCT/FI2007/000029, dated May 25, 2007.

* cited by examiner

*Primary Examiner* — Rei-tsang Shiao
(74) *Attorney, Agent, or Firm* — Finnegan, Henderson, Farabow, Garrett & Dunner, LLP

(57) ABSTRACT

New processes for manufacturing entacapone are provided.

14 Claims, No Drawings

PROCESS FOR MANUFACTURING ENTACAPONE

This application is a national stage filing under 35 U.S.C. §371 of International Application No. PCT/FI2007/000029, filed on Feb. 6, 2007, which claims the benefit of priority of U.S. Provisional Application No. 60/765,196 filed on Feb. 6, 2006. The contents of each application are incorporated herein by reference.

The present invention relates to a new process for manufacturing entacapone.

BACKGROUND OF THE INVENTION

Entacapone (E-N,N-diethyl-2-cyano-3-(3,4-dihydroxy-5-nitrophenyl)acrylamide) is a catechol-O-methyl transferase (COMT) inhibitor often used in combination with levodopa and a dopa decarboxylase (DDC) inhibitor in the treatment of Parkinson's disease. Entacapone is commercially available in a stand-alone formulation under the trademarks Comtess® and Comtan®, and under trademark Stalevo® in a fixed combination (levodopa:carbidopa:entacapone: 50 mg:12.5 mg:200 mg, 100 mg:25 mg:200 mg and 150 mg:37.5 mg:200 mg).

U.S. Pat. No. 5,446,194 discloses a method for the preparation of N,N-diethyl-2-cyano-3-(3,4-dihydroxy-5-nitrophenyl)acrylamide by refluxing a solution containing 3,4-dihydroxy-5-nitrobenzaldehyde, N,N-diethyl-2-cyanoacetamide and a catalytic amount of piperidine acetate in dry ethanol. The yield of said method is 73%. The product is a crude mixture of the E and Z isomers of N,N-diethyl-2-cyano-3-(3,4-dihydroxy-5-nitrophenyl)acrylamide having a melting point of 153° C.-156° C. The condensation reaction used in U.S. Pat. No. 5,446,194 is called a Knoevenagel condensation.

U.S. Pat. No. 5,135,950 discloses a process for the preparation of a stable and crystallographically essentially pure polymorphic form A of E-N,N-diethyl-2-cyano-3-(3,4-dihydroxy-5-nitrophenyl)acrylamide having a melting point of 162° C.-163° C. Said process comprises crystallization of the above described crude mixture of the E and Z isomers of N,N-diethyl-2-cyano-3-(3,4-dihydroxy-5-nitrophenyl)acrylamide from a lower aliphatic carboxylic acid containing a catalytic amount of hydrochloric or hydrobromic acid. The yield of said crystallographically pure polymorphic form A is 70-80%.

WO 2005/070881 purports to disclose a process for manufacturing the stable polymorphic form A of E-N,N-diethyl-2-cyano-3-(3,4-dihydroxy-5-nitrophenyl)acrylamide without isolating a crude solid isomeric mixture of N,N-diethyl-2-cyano-3-(3,4-dihydroxy-5-nitrophenyl)acrylamide. In said method, the Knoevenagel condensation step is carried out in an alcohol such as methanol, ethanol, isopropanol, isobutanol, n-butanol, preferably isopropanol, at reflux temperature in the presence of a suitable organic base such as piperidine, N-methylmorpholine, pyridine, piperazine etc., preferably piperidine base. After the completion of the reaction, the mixture is poured into a mixture of chilled water and ethyl acetate. The pH of the solution is adjusted to between 3.5 and 4.0 by adding acid. The ethyl acetate layer is separated, washed with water and concentrated to obtain the (E)-isomer of polymorphic form A. A serious drawback of the method disclosed in WO 2005/070881 is that the total yield of the process is low, as the (Z)-isomer (about 30%) formed during the reaction is not recovered and remains in the reaction solution, thus interfering with the crystallization of the E-isomer.

WO 2005/063696 purports to disclose a method for producing N,N-diethyl-2-cyano-3-(3,4-dihydroxy-5-nitrophenyl)acrylamide by heating 3,4-dihydroxy-5-nitrobenzaldehyde, raw N,N-diethyl-2-cyanoacetamide, acetic acid and diethyl amine in toluene, and by removing the water formed during the reaction through azeotropic distillation. A significant drawback of this method is that a large amount of solvent has to be used.

SUMMARY OF THE INVENTION

Applicants have discovered a process for manufacturing entacapone, which is industrially applicable due to its good quality and yield, controllability, and use of desirably low amounts of reagents and/or solvents.

One aspect of the invention is a process for manufacturing E-N,N-diethyl-2-cyano-3-(3,4-dihydroxy-5-nitrophenyl)acrylamide (entacapone), comprising:
a) reacting 3,4-dihydroxy-5-nitrobenzaldehyde with N,N-diethyl-2-cyanoacetamide in the presence of a catalyst in a C 4 to 8 alcohol at reduced pressure and at a temperature of at least 70° C.;
b) optionally cooling the resulting mixture from step a);
c) optionally seeding the resulting mixture from step a) or step b) with N,N-diethyl-2-cyano-3-(3,4-dihydroxy-5-nitrophenyl)acrylamide comprising at least 60% of the E-isomer by weight in the seeding crystals;
d) cooling the resulting mixture from step a) or step b) or step c) to a temperature of 30° C. or below;
e) seeding the cooled mixture from step d) with N,N-diethyl-2-cyano-3-(3,4-dihydroxy-5-nitrophenyl)acrylamide comprising at least 10% of the Z-isomer by weight in the seeding crystals;
f) cooling the mixture from step e) to a temperature of 5° C. or below;
g) isolating the crystallized product from the mixture; and
h) converting the obtained mixture of E- and Z-isomers of N,N-diethyl-2-cyano-3-(3,4-dihydroxy-5-nitrophenyl)acrylamide to the E-isomer of N,N-diethyl-2-cyano-3-(3,4-dihydroxy-5-nitrophenyl)acrylamide.

Additional aspects and advantages of the invention will be set forth in part in the description which follows, and in part will be obvious from the description, or may be learned by the practice of the invention. The objects and the advantages of the invention will be realized and attained by means of the elements and combinations particularly pointed out in the appended claims.

It is to be understood that both the foregoing general description and the following detailed description are exemplary and explanatory only and do not restrict the invention, as claimed.

DETAILED DESCRIPTION OF THE INVENTION

The applicants have now found that it is possible to manufacture entacapone with a good yield through a process, which is easy to control, and does not necessitate the use of large amounts of reagents including catalysts and/or solvents.

The process of the invention comprises the following steps:
a) reacting 3,4-dihydroxy-5-nitrobenzaldehyde with N,N-diethyl-2-cyanoacetamide in the presence of a catalyst in a C 4 to 8 alcohol at reduced pressure and at a temperature of at least 70° C.;
b) optionally cooling the resulting mixture from step a);
c) optionally seeding the resulting mixture from step a) or step b) with N,N-diethyl-2-cyano-3-(3,4-dihydroxy-5- nitrophenyl)acrylamide comprising at least 60% of the E-isomer by weight in the seeding crystals;

d) cooling the resulting mixture from step a) or step b) or step c) to a temperature of 30° C. or below;

e) seeding the cooled mixture from step d) with N,N-diethyl-2-cyano-3-(3,4-dihydroxy-5-nitrophenyl)acrylamide comprising at least 10% of the Z-isomer by weight in the seeding crystals;

f) cooling the mixture from step e) to a temperature of 5° C. or below;

g) isolating the crystallized product from the mixture; and h) converting the obtained mixture of E- and Z-isomers of N,N-diethyl-2-cyano-3-(3,4-dihydroxy-5-nitrophenyl) acrylamide to the E-isomer of N,N-diethyl-2-cyano-3-(3,4-dihydroxy-5-nitrophenyl)acrylamide.

Representative Embodiments

The reaction between 3,4-dihydroxy-5-nitrobenzaldehyde and N,N-diethyl-2-cyanoacetamide is carried out in a straight or branched chained C4 to C8 alcohol, such as n-butanol or isoamyl alcohol. Performed under reduced pressure (i.e., less than atmospheric pressure), the reaction may be carried out, for example, at a pressure of 80 kPa or below, or at a pressure of from 10 to 80 kPa. The reaction takes place at a temperature of at least 70° C. For instance, the reaction temperature may be from 70 to 115° C., from 75 to 105° C., or from 80 to 85° C.

The reaction between 3,4-dihydroxy-5-nitrobenzaldehyde and N,N-diethyl-2-cyanoacetamide is carried out in the presence of a catalyst, such as organic amines and/or salts thereof. Example catalysts include one or more of methylamine hydrochloride, piperidine, N-methylmorpholine, pyridine and piperazine. For instance, the reaction may be carried out in the presence of methylamine hydrochloride and piperidine, in the presence at least one organic amine and at least one organic acid, e.g. in the presence of piperidine and acetic acid, in the presence of methylamine, piperidine and acetic acid, or in the presence of piperidine and formic acid.

In one embodiment of the invention, the reaction between 3,4-dihydroxy-5-nitrobenzaldehyde and N,N-diethyl-2-cyanoacetamide is facilitated using water separation. Different techniques may be used to achieve water separation, such as azeotropic distillation and Dean Stark water separation. Water separation may also be achieved by adding to the reaction mixture one or more components capable of absorbing water, such as molecular sieves, carbonates or sulphates of alkali earth metals or alkali metals. In a similar way, one or more components capable of removing water through a chemical reaction such as carbodiimides, e.g. cyclohexylcarbodiimides may be added.

The reaction may take place over a time period sufficient to react 3,4-dihydroxy-5-nitrobenzaldehyde with N,N-diethyl-2-cyanoacetamide. Example reaction times include from 45 minutes to 10 hours, from 45 minutes to 6 hours, or from 2 hours to 5 hours.

The mixture produced from reaction step a) is optionally cooled in step b), for example, cooled to a temperature of from 70 to 75° C. The mixture produced from reaction step a), or the optionally cooled mixture from step b), may be optionally seeded in step c) with N,N-diethyl-2-cyano-3-(3,4-dihydroxy-5-nitrophenyl)acrylamide comprising at least 60% of the E-isomer in the seeding crystals. In one embodiment, the amount of the E-isomer in optional step c) is from 65 to 100% of the seeding crystals.

The mixture produced from reaction step a), or the optionally cooled mixture from step b), or the optionally seeded mixture from step c), is then cooled in step d) to a temperature of 30° C. or below, for example to a temperature of from 25 to 30° C. In one embodiment, the mixture is cooled in step d) to a temperature of from 25 to 30° C. and the cooling rate is from 10 to 30° C. per hour.

The cooled mixture from step d) is then seeded in step e) with N,N-diethyl-2-cyano-3-(3,4-dihydroxy-5-nitrophenyl) acrylamide comprising at least 10% of the Z-isomer in the seeding crystals. In one embodiment, the amount of the Z-isomer in step e) is from 20 to 100% of the seeding crystals.

In step f) of the invention, the seeded mixture from step e) is cooled to a temperature of 5° C. or below, for example to a temperature of from −5 to 5° C. In one embodiment, the mixture is cooled in step f) at a cooling rate of from 2 to 20° C. per hour, or at a cooling rate of from 3 to 10° C. per hour.

The isolation of step g) may be carried out using any isolation procedure used to isolate solids from liquids, for instance filtering. The isolated solid is then washed. The purpose of the washing is to replace the impure liquid in the filtering cake and to separate the catalyst and possible other agents, for instance water removing agents, from the product. In case organic amines are used as catalysts (as opposed to their salts), the removal of the catalyst may be facilitated by acidifying the reaction mixture before the isolation.

In step h) of the invention, the mixture of the Z- and E-isomers of N,N-diethyl-2-cyano-3-(3,4-dihydroxy-5-nitrophenyl)acrylamide is converted to the E-isomer. In one embodiment, the mixture is converted to a crystallographically essentially pure polymorph A of the E-isomer having principal X-Ray powder diffraction (XRD) peaks at 9.0, 21.9 and 23.3 when performed by Diffractomer Philips X'Pert PRO (PANalytical). A copper target X-ray (wavelength 0.1541 nm) tube was operated with the power of 45 kV×40 mA. A real time multiple strip detector X'Celerator was used. Polymorph A may be made, for instance, as disclosed in U.S. Pat. No. 5,135,950 which is incorporated herein by reference.

In one embodiment, the mixture is converted to the polymorph D of the E-isomer having principal XRD peaks at 6.8, 24.6 and 27.4 when measured using the same equipment and conditions as above. Polymorph D may be prepared by several methods, for instance, those disclosed in WO 2005/066117 and WO 2005/063696 incorporated herein by reference.

One representative embodiment of the invention comprises the following steps:

a) reacting 3,4-dihydroxy-5-nitrobenzaldehyde with N,N-diethyl-2-cyanoacetamide in the presence of at least one organic amine and/or its salt in n-butanol at a temperature of from 80 to 85° C.;

b) optionally neutralizing the organic amine and/or cooling the resulting mixture to a temperature of from 70 to 75° C.;

c) optionally seeding the resulting mixture from step b) with N,N-diethyl-2-cyano-3-(3,4-dihydroxy-5-nitrophenyl)acrylamide comprising from 60 to 100% of the E-isomer by weight in the seeding crystals d) cooling the resulting mixture from step c) to a temperature of from 25 to 30° C.;

e) seeding the cooled mixture from step d) with N,N-diethyl-2-cyano-3-(3,4-dihydroxy-5-nitrophenyl)acrylamide comprising from 10% to 100% of the Z-isomer by weight in the seeding crystals;

f) cooling the mixture from step e) to a temperature of from −5 to 5° C.;

g) isolating the crystallized product from the mixture; and h) converting the obtained mixture of E- and Z-isomers of N,N-diethyl-2-cyano-3-(3,4-dihydroxy-5-nitrophenyl) acrylamide to the E-isomer of N,N-diethyl-2-cyano-3-(3,4-dihydroxy-5-nitrophenyl)acrylamide.

Another representative embodiment of the invention comprises the following steps:
a) reacting 3,4-dihydroxy-5-nitrobenzaldehyde with N,N-diethyl-2-cyanoacetamide in the presence of at least one organic amine and/or its salt in isoamyl alcohol at a temperature of from 85 to 95° C.;
b) optionally neutralizing the organic amine and/or cooling the resulting mixture to a temperature of from 70 to 75° C.;
c) optionally seeding the resulting mixture from step b) with N,N-diethyl-2-cyano-3-(3,4-dihydroxy-5-nitrophenyl)acrylamide comprising from 60 to 100% of the E-isomer by weight in the seeding crystals;
d) cooling the resulting mixture from step c) to a temperature of from 25 to 30° C.;
e) seeding the cooled mixture from step d) with N,N-diethyl-2-cyano-3-(3,4-dihydroxy-5-nitrophenyl)acrylamide comprising from 10% to 100% of the Z-isomer by weight in the seeding crystals;
f) cooling the mixture from step e) to a temperature of from −5 to 5° C.;
g) isolating the crystallized product from the mixture; and
h) converting the obtained mixture of E- and Z-isomers of N,N-diethyl-2-cyano-3-(3,4-dihydroxy-5-nitrophenyl)acrylamide to the E-isomer of N,N-diethyl-2-cyano-3-(3,4-dihydroxy-5-nitrophenyl)acrylamide.

In one embodiment of the above-described two representative processes, a mixture of an organic amine and a salt of another organic amine is used in step a), wherein said organic amine is piperidine and the salt is methylamine hydrochloride.

If an organic amine is used in step a) (as opposed to its salt) it is possible to facilitate its later removal by neutralizing it after the completion of the reaction (e.g. in step b), for example by adding first water and then an acid (or an aqueous mixture of an acid), for instance a strong acid such as sulphuric acid or hydrochloric acid.

As mentioned above, entacapone is a catechol-O-methyl transferase (COMT) inhibitor that can be used in combination with levodopa and a dopa decarboxylase (DDC) inhibitor to treat Parkinson's disease. The pharmacologically effective amount of entacapone is dependent on numerous factors known to those skilled in the art, such as, the severity of the condition of the patient, the frequency and the desired duration of use, etc. The amount of entacapone in an appropriate formulation is typically from 25 to 400 mg, e.g. 25 to 300 mg, especially 50 to 200 mg.

All levodopa+carbidopa (or benserazide respectively) combinations may be used together with the entacapone manufactured according to the process of the invention. They are commercially available as combination tablets sold in Europe under, for instance, the following trademarks: Nacom® (distributed by X), Sinemet® (distributed by X). Levodopa and benserazide are commercially available as combination tablet in Europe under the trademark Madopar® (distributed by Roche).

The invention will be further clarified by the following non-limiting examples.

EXAMPLES

Example 1

Mixture of the E and Z Isomers of N,N-diethyl-2-cyano-3-(3,4-dihydroxy-5-nitrophenyl)acrylamide A vessel is charged with 240 ml of n-butanol, 120 g of 3,4-dihydroxy-5-nitrobenzaldehyde, 4.8 g of methylamine hydrochloride, 122 g of N,N-diethylcyanoacetamide and 7.2 ml of piperidine. The temperature is raised using water separation under vacuum to about 82° C. and the reaction mixture is boiled at this temperature using water separation for 4 hours. The reaction is followed using HPLC.

After completing the reaction 240 ml of hot water is added to the reaction mixture and 2.4 ml of strong sulphuric acid is added.

The reaction mixture is cooled to a temperature of 75° C. and seeded with crude N,N-diethyl-2-cyano-3-(3,4-dihydroxy-5-nitrophenyl)acrylamide (comprises 70% by weight of the E-isomer). After seeding the mixture is cooled to about 28° C. within 3 hours, during which time the E isomer crystallizes.

The reaction mixture is seeded with a mixture of the E and Z isomers of N,N-diethyl-2-cyano-3-(3,4-dihydroxy-5-nitrophenyl)acrylamide (comprises about 30% by weight of the Z-isomer) and mixed at about 28° C. for two hours. Thereafter the mixture is cooled slowly to 0° C. during which time the Z isomer crystallizes.

The mixture is filtered and washed twice with 60 ml of cold water and the filtering cake is dried. The yield is about 90% and the purity over 99.5%.

Example 2

Mixture of the E and Z Isomers of N,N-diethyl-2-cyano-3-(3,4-dihydroxy-5-nitrophenyl)acrylamide A vessel is charged with 180 ml of n-butanol, 120 g of 3,4-dihydroxy-5-nitrobenzaldehyde, 2.9 g of methylamine hydrochloride, 110 g of N,N-diethylcyanoacetamide and 4.3 ml of piperidine. The temperature is raised using water separation under vacuum to about 82° C. and the reaction mixture is boiled at this temperature using water separation for 5 hours. The reaction is followed using HPLC.

After completing the reaction 180 ml of hot water is added to the reaction mixture and 12 ml of strong sulphuric acid is added.

The reaction mixture is cooled to a temperature of 75° C. and seeded with crude N,N-diethyl-2-cyano-3-(3,4-dihydroxy-5-nitrophenyl)acrylamide (comprises 70% by weight of the E-isomer). After seeding the mixture is cooled to about 28° C. within 2 hours, during which time the E isomer crystallizes.

The reaction mixture is seeded with a mixture of the E and Z isomers of N,N-diethyl-2-cyano-3-(3,4-dihydroxy-5-nitrophenyl)acrylamide (comprises about 30% by weight of the Z-isomer) and mixed at about 28° C. for two hours. Thereafter the mixture is cooled slowly to 0° C. during which time the Z isomer crystallizes.

The mixture is filtered and washed twice with 100 ml of cold water and the filtering cake is dried. The yield is about 96% and the purity over 99.5%.

Example 3

Mixture of the E and Z Isomers of N,N-diethyl-2-cyano-3-(3,4-dihydroxy-5-nitrophenyl)acrylamide A vessel is charged with 100 ml of isoamylalcohol (3-methyl-butanol), 50 g of 3,4-dihydroxy-5-nitrobenzaldehyde, 2 g of methylamine hydrochloride, 50 g of N,N-diethylcyanoacetamide and 3 ml of piperidine. The temperature is raised using water separation under vacuum to about 90° C. and the reaction mixture is boiled at this temperature using water separation for 3 hours. The reaction is followed using HPLC.

After completing the reaction 220 ml of hot water is added to the reaction mixture and 1 ml of strong sulphuric acid is added.

The reaction mixture is cooled to a temperature of 75° C. and seeded with crude N,N-diethyl-2-cyano-3-(3,4-dihydroxy-5-nitrophenyl)acrylamide (comprises 70% by weight of the E-isomer). After seeding the mixture is cooled to about 28° C. within 2 hours, during which time the E isomer crystallizes.

The reaction mixture is seeded with a mixture of the E and Z isomers of N,N-diethyl-2-cyano-3-(3,4-dihydroxy-5-nitrophenyl)acrylamide (comprises about 30% by weight of the Z-isomer) and mixed at about 28° C. for two hours. Thereafter the mixture is cooled to 0° C. during which time the Z isomer crystallizes.

The mixture is filtered and washed with 120 ml of cold water and the filtering cake is dried. The yield is 77.58 g (93.1% of the theoretical yield). HPLC purity of the product is over 99%.

Example 4

Mixture of the E and Z Isomers of N,N-diethyl-2-cyano-3-(3,4-dihydroxy-5-nitrophenyl)acrylamide A vessel is charged with 100 ml of isoamylalcohol (3-methyl-butanol), 50 g of 3,4-dihydroxy-5-nitrobenzaldehyde, 2 g of methylamine hydrochloride, 50 g of N,N-diethylcyanoacetamide and 3 ml of piperidine. The temperature is raised using water separation under vacuum to about 89° C. and the reaction mixture is boiled at this temperature using water separation for 3 hours. The reaction is followed using HPLC.

After completing the reaction 220 ml of hot water is added to the reaction mixture and 1 ml of strong sulphuric acid is added.

The reaction mixture is cooled to a temperature of 75° C. and seeded with crude N,N-diethyl-2-cyano-3-(3,4-dihydroxy-5-nitrophenyl)acrylamide (comprises 70% by weight of the E-isomer). After seeding the mixture is cooled to about 28° C. within 2 hours, during which time the E isomer crystallizes.

The reaction mixture is seeded with a mixture of the E and Z isomers of N,N-diethyl-2-cyano-3-(3,4-dihydroxy-5-nitrophenyl)acrylamide (comprises about 30% by weight of the Z-isomer) and mixed at about 28° C. for two hours. Thereafter the mixture is cooled to 0° C. during which time the Z isomer crystallizes.

The mixture is filtered and washed with 120 ml of cold water and the filtering cake is dried. The yield is 79.0 g (94.8% of the theoretical yield). HPLC purity of the product is over 99%.

We claim:

1. A process for manufacturing E-N,N-diethyl-2-cyano-3-(3,4-dihydroxy-5-nitrophenyl) acrylamide, comprising:
   a) reacting 3,4-dihydroxy-5-nitrobenzaldehyde with N,N-diethyl-2-cyanoacetamide in the presence of a catalyst in a C4 to C8 alcohol at reduced pressure and at a temperature of at least 70° C.;
   b) optionally cooling the resulting mixture from step a);
   c) optionally seeding the resulting mixture from step a) or step b) with N,N-diethyl-2-cyano-3-(3,4-dihydroxy-5-nitrophenyl)acrylamide comprising at least 60% of the E-isomer by weight in the seeding crystals;
   d) cooling the mixture from step a) or step b) or step c) to a temperature of 30° C. or below;
   e) seeding the cooled mixture from step d) with N,N-diethyl-2-cyano-3-(3,4-dihydroxy-5-nitrophenyl)acrylamide comprising at least 10% of the Z-isomer by weight in the seeding crystals;
   f) cooling the mixture from step e) to a temperature of 5° c or below;
   g) isolating the crystallized product from the mixture; and
   h) converting the obtained mixture of the E- and Z-isomers of N,N-diethyl-2-cyano-3-(3,4-dihydroxy-5-nitrophenyl)acrylamide to the E-isomer of N,N-diethyl-2-cyano-3-(3,4-dihydroxy-5-nitrophenyl)acrylamide.

2. The process according to claim 1, wherein the C4 to C8 alcohol is n-butanol.

3. The process according to claim 1, wherein the reduced pressure is a pressure of 80 kPa or below.

4. The process according to claim 1, wherein the reaction temperature is from 70 to 105° C.

5. The process according to claim 1, wherein the catalyst comprises methylamine hydrochloride and piperidine.

6. The process according to claim 1, which comprises separating water from the reaction mixture during the reaction.

7. The process according to claim 1, wherein the reaction is carried out within a time period of from 45 minutes to 6 hours.

8. The process according to claim 1, wherein the mixture from step a) is cooled in a step b) to a temperature of from 70 to 75° C.

9. The process according to claim 1, wherein the mixture from step a) or step b) is seeded in a step c) with from 65 to 100% by weight of the E-isomer.

10. The process according to claim 1, wherein the mixture from step a) or step b) or step c) is cooled in step d) to a temperature of from 25 to 30° C.

11. The process according to claim 1, wherein the mixture is cooled in step f) to a temperature of −5 to 5° C.

12. The process according to claim 1, wherein the mixture is seeded in step e) with from 20 to 100% by weight of the Z-isomer.

13. The process according to claim 1, wherein the mixture is converted in step h) to a crystallographically essentially pure polymorph A of the E-isomer.

14. A process for manufacturing E-N,N-diethyl-2-cyano-3-(3,4-dihydroxy-5-nitrophenyl)acrylamide, comprising:
   a) reacting 3,4-dihydroxy-5-nitrobenzaldehyde with N,N-diethyl-2-cyanoacetamide in the presence of at least one organic amine and/or its salt in n-butanol at a temperature of from 80 to 85° C.;
   b) optionally neutralizing the organic amine and/or cooling the resulting mixture to a temperature of from 70 to 75° C.;
   c) optionally seeding the resulting mixture from step b) with N,N-diethyl-2-cyano-3(3,4-dihydroxy-5-nitrophenyl)acrylamide comprising from 60 to 100% of the E-isomer by weight in the seeding crystals;
   d) cooling the resulting mixture from step c) to a temperature of from 25 to 30° C.;
   e) seeding the cooled mixture from step d) with N,N-diethyl-2-cyano-3-(3,4-dihydroxy-5-nitrophenyl)acrylamide comprising from 10% to 100% of the Z-isomer by weight in the seeding crystals;
   f) cooling the mixture from step e) to a temperature of from −5 to 5° C.;
   g) isolating the crystallized product from the mixture; and
   h) converting the obtained mixture of E- and Z-isomers of N,N-diethyl-2-cyano-3(3,4-dihydroxy-5-nitrophenyl)acrylamide to the E-isomer of N,N-diethyl-2-cyano-3(3,4-dihydroxy-5-nitrophenyl)acrylamide.

* * * * *